(12) United States Patent
Ferguson et al.

(10) Patent No.: US 8,766,794 B2
(45) Date of Patent: Jul. 1, 2014

(54) HANDHELD FIELD MAINTENANCE TOOL WITH IMPROVED LOCATIONAL AWARENESS FUNCTIONALITY

(75) Inventors: Anthony D. Ferguson, Minnetrista, MN (US); Christopher P. Kantzes, Minneapolis, MN (US); Brad N. Mathiowetz, Lakeville, MN (US); Todd M. Toepke, Eden Prairie, MN (US); Kun Yang, Eden Prairie, MN (US); Adam E. Lund, St. Louis Park, MN (US); Donald R. Lattimer, Chaska, MN (US); Brian A. Franchuk, Richfield, MN (US)

(73) Assignee: Fisher-Rosemount Systems, Inc., Round Rock, TX (US)

( * ) Notice: Subject to any disclaimer, the term of this patent is extended or adjusted under 35 U.S.C. 154(b) by 240 days.

(21) Appl. No.: 13/191,623

(22) Filed: Jul. 27, 2011

(65) Prior Publication Data

US 2012/0040698 A1    Feb. 16, 2012

Related U.S. Application Data

(60) Provisional application No. 61/368,477, filed on Jul. 28, 2010.

(51) Int. Cl.
*G08B 1/08*    (2006.01)
(52) U.S. Cl.
USPC ............. 340/539.13; 340/539.16; 340/539.11
(58) Field of Classification Search
USPC .......... 455/457; 370/310; 700/83; 273/148 B; 702/183; 463/37, 46; 340/539.13, 340/539.16, 539.22–539.23, 539.1, 539.11
See application file for complete search history.

(56) References Cited

U.S. PATENT DOCUMENTS

| | | | |
|---|---|---|---|
| 5,195,392 A | 3/1993 | Moore et al. | 73/866.5 |
| 5,309,351 A | 5/1994 | McCain et al. | 364/132 |
| 5,442,639 A | 8/1995 | Crowder et al. | 371/20.1 |
| 5,823,831 A * | 10/1998 | Bowater et al. | 439/773 |

(Continued)

FOREIGN PATENT DOCUMENTS

| | | |
|---|---|---|
| CN | 101763576 | 6/2010 |
| DE | 10245176 | 4/2004 |

(Continued)

OTHER PUBLICATIONS

Invitation to Pay Additional Fees for international patent application No. PCT/US2010/034889 dated Sep. 15, 2010.

(Continued)

*Primary Examiner* — Daniel Previl
(74) *Attorney, Agent, or Firm* — Kelly, Holt & Christenson, PLLC

(57) ABSTRACT

A handheld field maintenance tool is provided. The tool includes, among other things, a wireless process communication protocol module configured to communicate in accordance with a wireless process communication protocol. The tool also includes a display and an input device. A controller is coupled to the wireless process communication protocol module, the display, and the input device. The controller is configured to generate a map on the display indicating a position of the handheld field maintenance device relative to at least one asset, such as a field device. The controller is further configured to determine a position of the handheld field maintenance device by triangulating using wireless process communication with a number of known, fixed-position wireless field devices.

32 Claims, 7 Drawing Sheets

(56) References Cited

U.S. PATENT DOCUMENTS

| | | | |
|---|---|---|---|
| 5,903,455 A | 5/1999 | Sharpe, Jr. et al. | 364/188 |
| 6,033,226 A | 3/2000 | Bullen | 434/219 |
| 6,211,649 B1 | 4/2001 | Matsuda | 320/115 |
| 6,236,223 B1 | 5/2001 | Brady et al. | 324/750.3 |
| 6,377,859 B1 | 4/2002 | Brown et al. | 700/79 |
| 6,633,782 B1 | 10/2003 | Schleiss et al. | 700/26 |
| 6,725,182 B2 | 4/2004 | Pagnano et al. | 702/188 |
| 6,971,063 B1 | 11/2005 | Rappaport et al. | 715/733 |
| 7,013,184 B2 | 3/2006 | Romagnoli et al. | 700/17 |
| 7,027,952 B2* | 4/2006 | DelaCruz et al. | 702/183 |
| 7,039,744 B2* | 5/2006 | Mathiowetz et al. | 710/305 |
| 7,054,695 B2* | 5/2006 | Opheim et al. | 700/83 |
| 7,120,391 B2 | 10/2006 | Stengele et al. | 455/41.3 |
| 7,188,200 B2 | 3/2007 | Griech | 710/100 |
| 7,337,369 B2 | 2/2008 | Barthel et al. | 714/43 |
| 7,400,255 B2 | 7/2008 | Horch | 340/572.7 |
| 7,454,252 B2 | 11/2008 | El-Sayed | 700/21 |
| 7,505,819 B2 | 3/2009 | El-Sayed | 700/21 |
| 7,506,812 B2 | 3/2009 | von Mueller et al. | 235/449 |
| 7,675,406 B2 | 3/2010 | Baier et al. | 340/506 |
| 7,733,833 B2 | 6/2010 | Kalika et al. | 370/338 |
| 7,797,061 B2 | 9/2010 | El-Sayed | 700/21 |
| 7,832,638 B2* | 11/2010 | Wetzel et al. | 235/385 |
| 8,000,815 B2 | 8/2011 | John et al. | 700/18 |
| 8,036,007 B2 | 10/2011 | Woehrle | 363/65 |
| 8,044,796 B1* | 10/2011 | Carr, Sr. | 340/539.13 |
| 8,059,101 B2 | 11/2011 | Westerman et al. | 345/101 |
| 8,060,862 B2 | 11/2011 | Eldridge et al. | 717/121 |
| 8,060,872 B2 | 11/2011 | Da Silva Neto | 717/177 |
| 8,074,172 B2 | 12/2011 | Kocienda et al. | 715/263 |
| 8,126,145 B1 | 2/2012 | Tewari et al. | 380/255 |
| 8,150,462 B2 | 4/2012 | Guenter et al. | 455/557 |
| 8,180,948 B2 | 5/2012 | Kreider et al. | 710/313 |
| 8,224,256 B2 | 7/2012 | Citrano, III et al. | 455/67.11 |
| 2001/0047504 A1 | 11/2001 | Aoyama | 714/799 |
| 2002/0004512 A1 | 1/2002 | Stengele et al. | 455/39 |
| 2002/0007237 A1 | 1/2002 | Phung et al. | 701/33 |
| 2002/0027504 A1 | 3/2002 | Davis et al. | 340/540 |
| 2002/0086642 A1 | 7/2002 | Ou et al. | 455/69 |
| 2002/0167904 A1 | 11/2002 | Borgeson et al. | 702/183 |
| 2002/0171558 A1 | 11/2002 | Bartelheim et al. | 340/825.49 |
| 2003/0050737 A1 | 3/2003 | Osann, Jr. | 700/276 |
| 2003/0109937 A1 | 6/2003 | Zielinski et al. | 700/1 |
| 2003/0204373 A1 | 10/2003 | Zielinski et al. | 702/184 |
| 2003/0229472 A1 | 12/2003 | Kantzes et al. | 702/183 |
| 2004/0039458 A1 | 2/2004 | Mathiowetz et al. | 700/17 |
| 2004/0111238 A1 | 6/2004 | Kantzes et al. | 702/183 |
| 2004/0193287 A1 | 9/2004 | Lefebvre et al. | 700/1 |
| 2004/0204193 A1 | 10/2004 | Li et al. | 455/575.1 |
| 2004/0228184 A1 | 11/2004 | Mathiowetz | 365/202 |
| 2004/0230327 A1 | 11/2004 | Opheim et al. | 700/83 |
| 2005/0114086 A1 | 5/2005 | Zielinski et al. | 702/183 |
| 2005/0164684 A1 | 7/2005 | Chen et al. | 455/414.1 |
| 2005/0222698 A1 | 10/2005 | Eryurek et al. | 700/90 |
| 2005/0223120 A1 | 10/2005 | Scharold et al. | |
| 2006/0014533 A1 | 1/2006 | Warren | 455/423 |
| 2006/0087402 A1 | 4/2006 | Manning et al. | 340/3.1 |
| 2006/0111955 A1* | 5/2006 | Winter et al. | 705/8 |
| 2006/0155908 A1 | 7/2006 | Rotvold et al. | 710/313 |
| 2006/0206277 A1 | 9/2006 | Horch | 702/82 |
| 2006/0290496 A1 | 12/2006 | Peeters | 340/572.1 |
| 2006/0291438 A1 | 12/2006 | Karschnia et al. | 370/338 |
| 2007/0161352 A1 | 7/2007 | Dobrowski et al. | 455/69 |
| 2007/0161371 A1 | 7/2007 | Dobrowski et al. | 455/423 |
| 2007/0179645 A1* | 8/2007 | Nixon et al. | 700/83 |
| 2007/0208279 A1 | 9/2007 | Panella et al. | 600/595 |
| 2008/0114911 A1 | 5/2008 | Schumacher | 710/72 |
| 2008/0234837 A1 | 9/2008 | Samudrala et al. | 700/19 |
| 2008/0268784 A1* | 10/2008 | Kantzes et al. | 455/66.1 |
| 2008/0313559 A1* | 12/2008 | Kulus et al. | 715/771 |
| 2009/0065578 A1 | 3/2009 | Peterson et al. | 235/382 |
| 2009/0094466 A1 | 4/2009 | Matthew et al. | 713/300 |
| 2009/0125713 A1 | 5/2009 | Karschnia et al. | 713/153 |
| 2009/0171483 A1 | 7/2009 | Scheuermann | 700/83 |
| 2009/0177970 A1 | 7/2009 | Jahl et al. | 715/735 |
| 2009/0271726 A1 | 10/2009 | Gavimath et al. | 715/771 |
| 2009/0284390 A1 | 11/2009 | Lahner et al. | 340/825.49 |
| 2009/0296601 A1 | 12/2009 | Citrano et al. | 370/254 |
| 2009/0326852 A1 | 12/2009 | Vetter et al. | 702/108 |
| 2010/0100766 A1 | 4/2010 | Bengtsson et al. | 714/23 |
| 2010/0114347 A1 | 5/2010 | Dheenathayalan et al. | 700/97 |
| 2010/0114549 A1 | 5/2010 | Kolavi | 703/13 |
| 2010/0145476 A1 | 6/2010 | Junk et al. | 700/7 |
| 2010/0220630 A1 | 9/2010 | Kalika et al. | 370/254 |
| 2010/0267359 A1* | 10/2010 | Gyllensvaan | 455/404.1 |
| 2010/0290084 A1 | 11/2010 | Russell, III et al. | 358/1.15 |
| 2010/0290351 A1 | 11/2010 | Toepke et al. | 370/250 |
| 2010/0290359 A1 | 11/2010 | Dewey et al. | 370/252 |
| 2010/0293363 A1 | 11/2010 | Meyer et al. | 713/1 |
| 2011/0117529 A1 | 5/2011 | Barash et al. | 434/265 |
| 2011/0238188 A1 | 9/2011 | Washiro | 700/19 |
| 2012/0038458 A1 | 2/2012 | Toepke et al. | 340/6.1 |
| 2012/0038548 A1 | 2/2012 | Toepke et al. | 345/156 |
| 2012/0038760 A1 | 2/2012 | Kantzes et al. | 348/61 |
| 2012/0040316 A1 | 2/2012 | Mathiowetz et al. | 434/219 |
| 2012/0041744 A1 | 2/2012 | Kantzes et al. | 703/13 |
| 2012/0046911 A1 | 2/2012 | Mathiowetz et al. | 702/184 |

FOREIGN PATENT DOCUMENTS

| | | |
|---|---|---|
| DE | 102007035158 | 1/2009 |
| DE | 102008029406 | 12/2009 |
| DE | 102009028195 | 2/2011 |
| EP | 1515208 | 3/2005 |
| EP | 1916582 | 4/2008 |
| EP | 2071427 | 6/2009 |
| EP | 2077473 | 7/2009 |
| EP | 2148259 | 1/2010 |
| EP | 2204705 | 7/2010 |
| GB | 2382418 | 5/2003 |
| GB | 2 394 124 | 4/2004 |
| JP | 9051583 | 2/1997 |
| JP | H1165641 | 3/1999 |
| JP | H11353332 | 12/1999 |
| JP | 2000092240 | 3/2000 |
| JP | 2001125633 | 5/2001 |
| JP | 2001337004 | 7/2001 |
| JP | 2003241829 | 8/2003 |
| JP | 2007-91381 | 4/2007 |
| JP | 2008165193 | 7/2008 |
| JP | 2009004977 | 1/2009 |
| JP | 2009036720 | 2/2009 |
| KR | 20060078883 | 7/2006 |
| WO | WO 01/35190 | 5/2001 |
| WO | WO 02/086662 | 10/2002 |
| WO | WO 2006/016845 | 2/2006 |
| WO | WO 2008/042074 | 4/2008 |
| WO | WO 2008/077358 | 7/2008 |
| WO | WO 2008/096216 | 8/2008 |
| WO | WO 2008/127632 | 10/2008 |
| WO | WO 2009/003146 | 12/2008 |
| WO | WO 2009/003148 | 12/2008 |
| WO | WO 2009/074544 | 6/2009 |

OTHER PUBLICATIONS

ABB Limited: "Wireless Instrumentation Jargon Buster". Information bulletin instrumentation ABB no IB/INST-018, Mar. 3, 2009, XP002596601. Retrieved from the Internet: URL:http://www05.abb.com/global/scot/scot203.nsf/veritydisplay/be00ec76ef07e978c125756e003157b9/$File/1B_INST_018_1.pdf.

Notification of Transmittal of the International Search Report and the Written Opinion from the International Application No. PCT/US2010/021764.

David Gustafsson: "WirelessHART—Implementation and Evaluation on Wireless Sensors". Masters's Degree Project, KTH University, Electrical Engineering, Apr. 1, 2009, pp. 1-39, XP002596602, Stockholm, Sweden. Retrieved from the Internet: URL:http://www.ee.kth.se/php/modules/publications/reports/2009/XR-EE-RT%202009:003.pdf.

(56) References Cited

OTHER PUBLICATIONS

Notification of Transmittal of the International Search Report and the Written Opinion for the International application No. PCT/US2010/034848 dated Aug. 26, 2010.
1420 Wireless Gateway: Product Data Sheet 00813-0100-4420, Rev BA Mar. 2008. Emerson Process Management.
Smart Wireless Gateway (WirelessHART™). Quick Installation Guide 00825-0200-4420, Rev BA. Aug. 2009. Emerson Process Management.
Rosemount 3051S Wireless Series Scalable Pressure, Flow, and Level Solutions. Reference Manual 00809-0100-4802, rev BA. Aug. 2007. Emerson Process Management.
EPO Communication pursuant to Rules 161(1) and 162 EPC for European patent application No. 10701430.0 dated Aug. 30, 2011.
Invitation to Pay Additional Fees for international patent application No. PCT/US2010/034949 dated Sep. 17, 2010.
Product Data Sheet: VIATOR RS232. MACTek Measurement and Control Technologies retrieved from www.mactekcorp.com/product1.htm.
Notification of Transmittal of the International Search Report and the Written Opinion from the International Application No. PCT/US2010/034889.
Notification of Transmittal of the International Search Report and the Written Opinion from the International Application No. PCT/US2010/034949.
EPO Communication from related European application No. 10730279.6 dated Jan. 13, 2012.
EPO Communication from related European application No. 10730281.2 dated Jan. 13, 2012.
EPO Communication from related European application No. 10725543.2 dated Jan. 12, 2012.
Rosemount 3051SMV Quick Installation Guide 00825-0100-4803 Rev BA. Apr. 2011.
Invitation to Pay Additional Fees from the International Application No. PCT/US2011/045673 dated Jan. 16, 2012.
Notification of Transmittal of the International Search Report and the Written Opinion from the International Application No. PCT/US2011/045680 dated Jul. 6, 2012.
Notification of Transmittal of the International Search Report and the Written Opinion from the International Application No. PCT/US2011/045681 dated Jan. 5, 2012.
475 Field Communicator. User's Guide XP007919976. Aug. 2009. www.fieldcommunicator.com by Emerson Process Management.
1420 Wireless Gateway. Reference Manual 00809-0100-4420, Rev BA. Aug. 2007. Emerson Process Management.
Invitation to pay additional Fees from the related international patent application No. PCT/US2011/045679 dated Aug. 6, 2012.
Invitation to pay additional fees from the related international patent application No. PCT/US2011/045664 dated Aug. 9 , 2012.
Invitation to pay additional fees from the related International patent application No. PCT/US2011/045676 dated Jul. 30, 2012.
International Search Report and Written Opinion from the related International patent application No. PCT/US2011/045665 dated Nov. 6, 2012.
First Communication from related European patent application No. 107255432 dated Oct. 11, 2012.
First Communication from related European patent application No. 107302796 dated Oct. 19, 2012.
Lee S W et al: "Honam Petrochemical Corporation Uses Simulator for Ethylene Plant Operator Training", Processing of the Industrial Computing Conference. Houston, Oct. 18-23, 1992. pp. 219-222.
Kurrle H-P et al.; "Trainingssimulator Zur Ausbildung Von Chemikanten und Anlagenfahrern. Otraining Simulator for the Training of Process Workers (Chemikanten) and Operators", Automatisierungstechnische Praxis—ATP, Oldenbourg Indusrieverlag, Munchen, DE, vol. 36, No. 7, Jul. 1, 1994. Abstract, Section 2.
Invitation to pay additional fees from the related International patent application No. PCT/US2011/045665 dated Aug. 23, 2012.
Bushman J B: "Ally: An Operator's Associate tbr Cooperative Supervisory Control Systems", IEEE Transactions on Systems, Man and Cybernetics. IEEE Inc. New York, US, vol. 23. No. 1. Jan. 1, 1993, pp. 111-128.
First Communication for the related European patent application No. 107302812 dated Oct. 11, 2012.
International Search Report and Written Opinion from the related international patent application No. PCT/US2011/045664 dated Nov. 6, 2012.
International Search Report and Written Opinion from the related International patent application No. PCT/US2011/045679 dated Nov. 6, 2012.
Office Action from related Russian application No. 2011151063 dated Nov. 12, 2012.
First Office Action from related Japanese application No. 2015511048, dated Jan. 29, 2013.
First Office Action from counterpart Japanese patent application No. 2013-521967, dispatched Feb. 25, 2014. 10 pages.

* cited by examiner

HANDHELD FIELD MAINTENANCE TOOL WITH IMPROVED LOCATIONAL AWARENESS FUNCTIONALITY

CROSS-REFERENCE TO RELATED APPLICATION

The present application is based on and claims the benefit of U.S. provisional patent application Ser. No. 61/368,477, filed Jul. 28, 2010, the content of which is hereby incorporated by reference in its entirety.

BACKGROUND

Handheld field maintenance tools are known. Such tools are highly useful in the process control and measurement industry to allow operators to conveniently communicate with and/or interrogate field devices in a given process installation. Examples of such process installations include petroleum, pharmaceutical, chemical, pulp, and other fluid processing installations. In such installations, the process control and measurement network may include tens or even hundreds of various field devices which periodically require maintenance to ensure that such devices are functioning properly and/or calibrated. Moreover, when one or more errors in the process control and measurement installation are detected, the use of a handheld field maintenance tool allows a technician to quickly diagnose such errors in the field. Handheld field maintenance tools are generally used to configure, calibrate, and diagnose problems relative to intelligent field devices using digital process communication protocols.

Since at least some process installations may involve highly volatile, or even explosive, environments, it is often beneficial, or even required, for field devices and the handheld field maintenance tools used with such field devices to comply with intrinsic safety requirements. These requirements help ensure that compliant electrical devices will not generate a source of ignition even under fault conditions. One example of Intrinsic Safety requirements is set forth in: APPROVAL STANDARD INTRINSICALLY SAFE APPARATUS AND ASSOCIATED APPARATUS FOR USE IN CLASS I, II and III, DIVISION NUMBER 1 HAZARDOUS (CLASSIFIED) LOCATIONS, CLASS NUMBER 3610, promulgated by Factory Mutual Research October, 1998. An example of a handheld field maintenance tool that complies with intrinsic safety requirements includes that sold under trade designation Model 475 Field Communicator, available from Emerson Process Management of Austin, Tex.

SUMMARY

A handheld field maintenance tool is provided. The tool includes, among other things, a wireless process communication protocol module configured to communicate in accordance with a wireless process communication protocol. The tool also includes a display and an input device. A controller is coupled to the wireless process communication protocol module, the display, and the input device. The controller is configured to generate a map on the display indicating a position of the handheld field maintenance device relative to at least one asset, such as a field device. The controller is further configured to determine a position of the handheld field maintenance device by triangulating using wireless process communication with a number of known, fixed-position wireless field devices.

A method of determining a physical location of an object using a handheld tool is also provided. The method includes creating an entry for an object in a database stored in the handheld tool. Placing the handheld tool in proximity to the object or using a display to move an object icon to an estimated location of the object. Receiving user input and responsively setting a physical position of the object associated with the entry for the object created in the database.

DETAILED DESCRIPTION

Figure 1A:
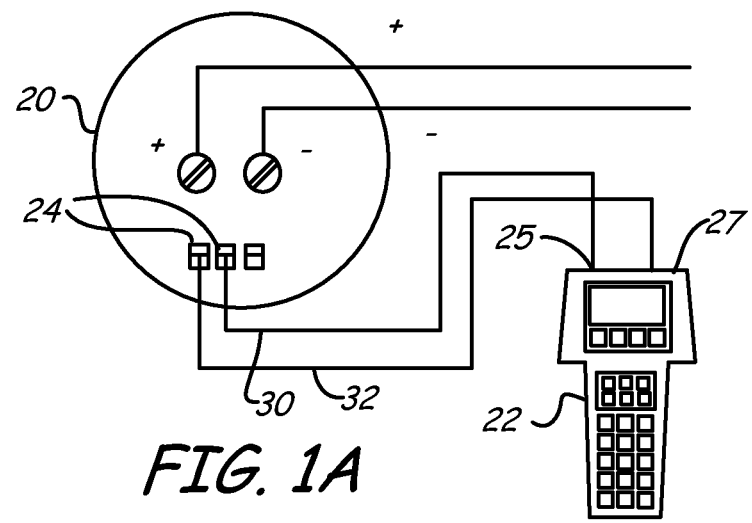
FIGS. 1A and 1B are diagrammatic views of a handheld field maintenance tool with which embodiments of the invention are particularly useful.
Figure 1B:
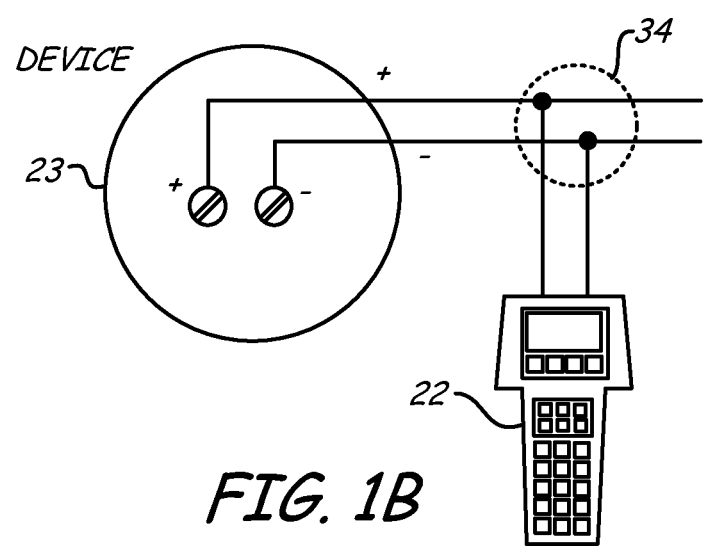

FIGS. 1A and 1B are diagrammatic views of a handheld field maintenance tool 22 coupled to field devices 20, 23. As shown in FIG. 1A, handheld field maintenance tool 22 includes a pair of terminals 25, 27 that couple to test leads 30, 32, respectively, which are then coupled to terminals 24 of field device 20. Terminals 24 may be dedicated terminals to allow such a handheld field maintenance tool to couple to device 20 and interact with device 20. The utilization of terminals 25, 27 to couple to field device illustrates an example of a wired connection between handheld field maintenance tool 22 and field device 20.

FIG. 1B shows an alternate arrangement where handheld field maintenance tool 22 couples directly to the process control loop 34 to which field device 23 is coupled. In either case, the wired connection between the handheld field maintenance tool and the field device allows the handheld field maintenance tool to interact with the desired field device 20, 23. As will be described in greater detail below, embodiments of the present invention are useful for locating any process installation assets or objects, including, but not limited to, field devices.

Figure 2:
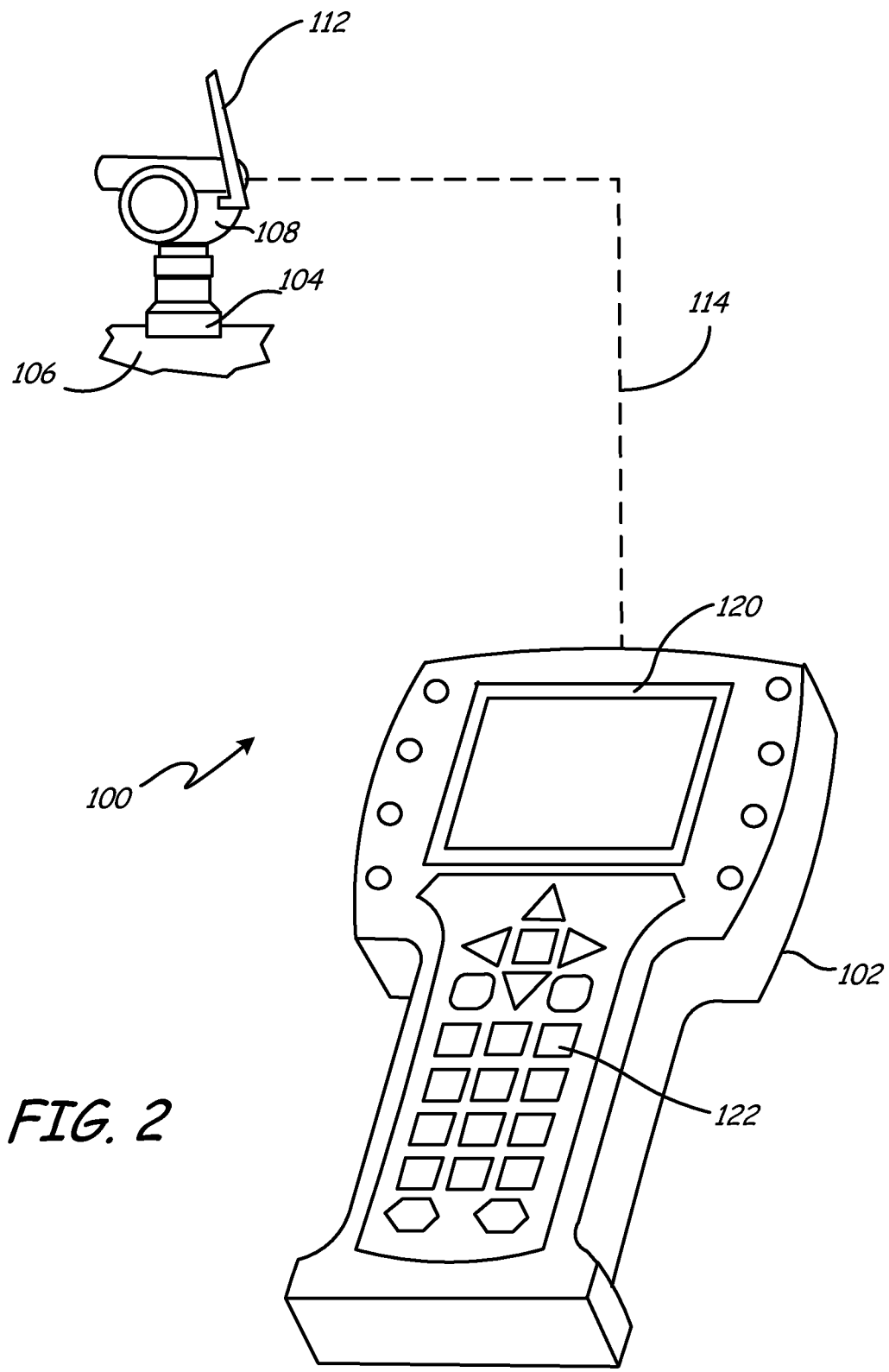
FIG. 2 is a diagrammatic view of a handheld field maintenance tool with which embodiments of the present invention are particularly useful.

FIG. 2 is a diagrammatic view of handheld field maintenance tool 102 interacting with wireless field device 104. System 100 includes handheld field maintenance tool 102 communicating with field device 104. Handheld field maintenance tool 102 is communicatively coupled to field device 104 via communication link 114. Communication link 114 can take any suitable form including wired connections as shown in FIGS. 1A and 1B, as well as wireless communication techniques that are currently being used or being developed. Handheld field maintenance tool 102 allows a technician to interact with field device 104 to configure, calibrate, and/or diagnose problems with respect to field device 104 using a digital process communication protocol such as FOUNDATION™ Fieldbus and/or the HART® protocol.

Handheld field maintenance tools, such as tool 102 can be used to save configuration data from field devices, such as field device 104. Embodiments of the present invention are also useful for communicating on a process installation bus where a number of field devices (such as 16+) communicate and differentiating one field device from others.

Field device 104 may be any device that senses a variable in the process and transmits information related to the variable over a process communication loop; such as a pressure or temperature. Field device 104 may also be a device that receives information from a process communication loop and sets a physical parameter, such as a valve closure, based on the information. Field device 104 is depicted as an industrial process fluid pressure transmitter having a pressure manifold 106 coupled thereto, and an electronics enclosure 108. Field device 104 is provided for illustrative purposes only. In reality, field device 104 may be any industrial device, such as a process fluid temperature transmitter, process fluid level transmitter, process fluid flow transmitter, valve controller, or any other device that is useful in the measurement and/or control of industrial processes.

Handheld field maintenance tool 102 generally includes a user interface that comprises a display 120 as well as a number of user input buttons 122. Display 120 may be any suitable display such as an active-matrix liquid crystal display, or any other suitable display that is able to provide useful information. Buttons 122 may comprise any suitable arrangement of buttons relative to any number of functions to which the handheld field maintenance tool may be directed. Buttons 122 may comprise a numeric keypad, an alphanumeric keypad, any suitable number of custom functions and/or navigation buttons, or any combination thereof.

Figure 3:
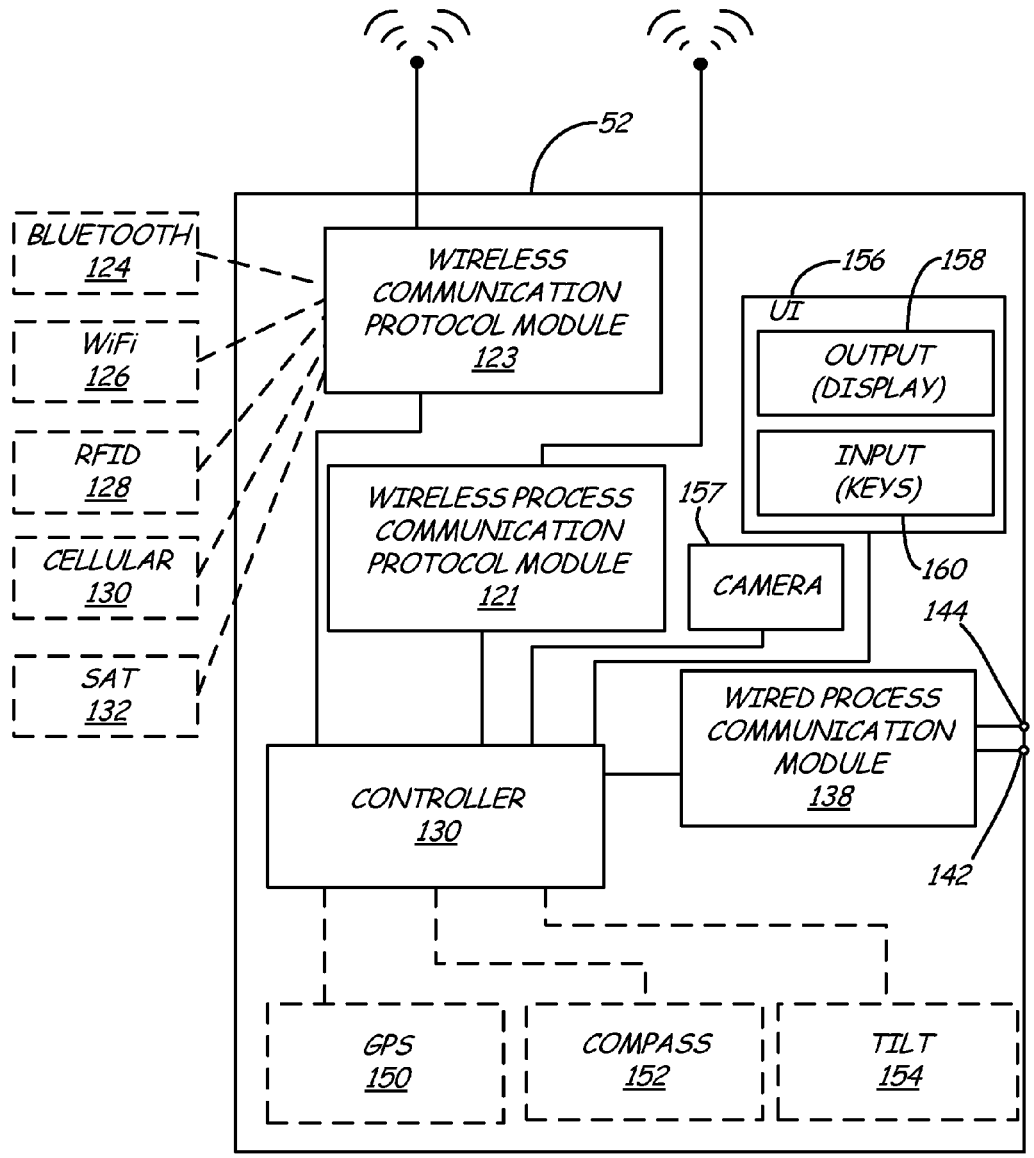
FIG. 3 is a block diagram of a handheld field maintenance tool in accordance with an embodiment of the present invention.

FIG. 3 is a diagrammatic system block diagram of a handheld field maintenance tool in accordance with the embodiment of the present invention. It is preferred that tool 52 comply with at least one intrinsic safety specification, such as that listed above, in order to help ensure safety in potentially explosive environments. Handheld field maintenance tool 52 includes at least one wireless process communication module 121. Suitable examples for wireless process communication module 121 include a module that generates and/or receives proper signals in accordance with a known wireless communication protocol, such as the known WirelessHART protocol (IEC 62591). Another wireless process communication protocol is set forth in ISA100.11a. While FIG. 3 shows a single wireless process communication module 121, it is expressly contemplated that any suitable number of wireless process communication modules can be used to communicate in accordance with various wireless process communication protocols now in existence or later developed. While embodiments of the present invention are generally described with respect to an intrinsically-safe handheld field maintenance tool that includes at least one process communication module, some embodiments may be practiced without process communication, using only GPS position information and a handheld tool.

Handheld field maintenance tool 52 also includes at least one secondary wireless communication protocol module 123. Wireless communication protocol module 123 can communicate in accordance with one or more of the options shown in phantom in FIG. 3. Specifically, wireless communication protocol module 123 may communicate in accordance with a Bluetooth specification 124 (such as Bluetooth Specification 2.1 rated at Power Class 2; a Wi-Fi specification 126 (such as IEEE 802.11.a/b/g/n); a known RFID specification 128; cellular communication techniques 130 (such as GSM/CDMA); and/or satellite communication 132. These communication techniques and methodologies allow handheld field maintenance tool 52 to communicate directly with a wireless gateway or other suitable device either via direct wireless communication, or using the Internet. While one wireless communication protocol module 123 is shown in FIG. 3, any suitable number may be used. Each of the wireless process communication protocol module 121 and wireless communication protocol module 123 is coupled to controller 130 which is also coupled to the wired process communication module 138. Controller 130 is preferably a microprocessor that executes a sequence of instructions stored therein, or in memory coupled to controller 130, to perform handheld field maintenance tasks. Wired process communication module 138 allows handheld field maintenance tool 52 to be physically coupled via a wired connection at terminals 142, 144 to a field device. Examples of suitable wired process communication include the highway addressable remote transducer (HART®) protocol, the FOUNDATION™ Fieldbus protocol, Profibus and others.

Handheld field maintenance tool 52 includes a user interface module 156 for generating a user interface using display 120 and keys 122. Module 156 can include suitable display driver circuitry 158 and/or memory to interact with display 120. Module 156 also includes input circuitry 160 which is configured to interact with buttons 122 to receive user input. Additionally, in embodiments where display 120 includes a touchscreen, module 160 can include circuitry to generate user input data to controller 130 based upon a user's touch and/or gestures received by the touchscreen.

Handheld field maintenance tool 52 can include a number of additional items that facilitate additional functionality. Specifically, tool 52 can include a position detection module, such as GPS module 150. GPS module 150 can be configured to additionally use the Wide Area Augmentation System (WAAS) for improved accuracy and/or can be configured to operate using differential GPS techniques as appropriate. Module 150 is coupled to controller 130 to provide controller 130 with an indication of the geographic position of tool 52. While position detection module 150 is preferably an internal component of tool 52, it may be external and communicatively coupled thereto using a suitable wireless or wired communication protocol, such as Bluetooth 124, RFID 128, et cetera. Further still, while position detection module 150 is generally described as GPS module 150, other techniques for triangulating the position of the handheld field maintenance tool based upon relative strength of wireless communication with wireless transceivers having known fixed positions can be employed. Examples of such wireless triangulation techniques include triangulation of the position of handheld field maintenance tool 52 based upon communication with three or more fixed-position WiFi communication points, or access points. Further still, as set forth above, embodiments of the present invention may include the ability to employ one or more wireless process communication protocol modules, such as module 121. Such triangulation techniques can also be employed if a suitable number of wireless interactions with fixed-position wireless field devices can be achieved. Finally, while the various methods provided for obtaining the position of handheld field maintenance tool 52 are described above, they can also be used in conjunction with one another to provide additional accuracy and/or redundancy. Additionally, tool 52 also preferably comprises compass module 152 coupled to controller 130 such that tool 52 can indicate the compass direction in which it is pointing. Finally, tool 52 can also include tilt module 154 coupled to controller 130 to provide an indication to controller 130 relative to an angle of inclination of tool 52 relative to gravity. However, additional axes of sensing are also contemplated.

The positional location module 150, compass module 152 and tilt module 154 are particularly useful where a handheld field maintenance tool helps a technician or engineer find the physical location of a wireless field device in the field. An oil refinery is often a very large process installation with many field devices positioned at various locations, some of which may not be readily visible. When a technician or engineer needs to physically locate a field device to perform engineering, setup and/or maintenance tasks, the technician or engineer would previously need to perform one of the following tasks. The technician or engineer would be forced to search for the field device based on memory or word-of-mouth directions from another technician or engineer. Alternatively, the technician or engineer would look up the field device in engineering drawings, which often do not contain detailed information about the physical location of the device. Then, based on that often limited information, the technician or engineer would attempt to physically locate the device in the plant or process installation.

Embodiments of the present invention generally utilize geographical information relative to a fixed-position field device, which information is loaded into, or otherwise created within a handheld field maintenance tool to allow the handheld field maintenance tool to help a user to navigate to the physical location of the field device. Moreover, in some embodiments, such location information may be transferred from one handheld field maintenance device to another such that another technician's handheld field maintenance tool can be updated with location information from a first technician's handheld field maintenance tool in order for both technicians to have the ability to quickly and easily find the navigate to the physical position of the field device. Preferably, this transfer of information between handheld field maintenance tools is performed wirelessly; however any suitable technique for transferring information between the handheld field maintenance tools can be employed.

As illustrated in FIG. 3, handheld field maintenance tool 52 preferably includes camera 157. Camera 157 is preferably disposed within handheld field maintenance tool 52, and is configured to acquire still and/or video images. Further, camera 157 can also be provided with an audio input such that real-time video recording with sound can be provided.

Embodiments of the present invention generally leverage the handheld field maintenance tool's ability to determine its own position in order to facilitate position-based field maintenance. Preferably, handheld field maintenance tool 52 uses GPS and/or cellular or WirelessHART triangulation to help a technician navigate to the position of a field device or process asset within a reasonable radius. The utilization of wireless signal triangulation (in additional to simply using GPS) is important since the industrial process environment generally interferes with traditional GPS signals/receivers. Thus, a position location module that is configured to use triangulation in place of or in combination with GPS is advantageous in a process installation. Further still, WirelessHART triangulation is specifically preferred due to the availability of multiple reference points (such as a number of fixed-positional wireless field devices) in close proximity to the asset.

In order to facilitate location-based field maintenance, each field device generally has its physical location assigned or otherwise determined when it is commissioned, or interacted with by a technician. One way in which a field maintenance technician can set the location of a device is for the handheld field maintenance technician to run or otherwise execute a software application stored in memory within controller 130, which application renders a map on display 120. The map will show the location of the handheld field maintenance tool as determined by position module 150. The technician can then move to a position as close to the field device as possible without losing the accuracy of the position detection signal (GPS/cellular/WirelessHART/WiFi) and then drag, or otherwise interact with, an icon representing the field device onto the map. If an entry for the field device does not already exist in a local database of the handheld field maintenance tool, an entry is created. The technician then moves the field device icon on the map in any direction and for any distance relative to the handheld field maintenance tool's current position until the technician is satisfied that the indicated position on the mini-map is a reasonable representation of the physical reality. Alternatively, the technician can simply move the handheld field maintenance tool to the position of the field device. Next, the technician selects the icon and sets the location within the handheld field maintenance tool. This stores the positional information representative of the handheld field maintenance tool's current position as modified by the technician's icon-based movement vector, if any.

The map rendered on display 120 can be any suitable pictorial representation of the position of the handheld field maintenance tool relative to a field device. The map is preferably two-dimensional, but may be three-dimensional. Additionally, the technician can also assign an altitude of the field device through data entry. The coordinate provided for altitude can be either positive (height above ground) or negative (depth below ground). The altitude parameter is used to cause the map icons to appear slightly different (such as transparent) even when the handheld field maintenance tool is at the same exact location as the field device to indicate to the technician that the field device is not at ground level. Preferably, the transparency varies with the distance from ground level. For example, the farther the field device is from the ground level, the more transparent the associated field device icon. Additionally or alternatively, the height parameter or altitude itself can be indicated next to or on the field device icon. Further still, any other suitable pictorial indication relative to the field device can be provided to indicate the height parameter. For example, the color of the field device icon can be varied from a first color, indicating depths below ground, to a second color indicating heights above ground. For non-communicating process assets, such as a large tank, the icon, or other suitable representation thereof, preferably indicates non-communication by virtue of an icon property. For example, a red icon may indicate a non-communicating process installation asset.

When the technician applies the field device location to the map, the handheld field maintenance tool may communicate with the field device through wired process communication module 138, or wireless process communication module 121, as may be appropriate, to assign positional coordinates (such as latitude, longitude, and altitude) to that field device. Alternatively, the handheld field maintenance tool can interact with an asset management system to update, or otherwise store, the positional information of the field device. Additionally, field devices that do not employ digital communication (such as conventional devices employing 4-20 mA signaling) can also be located by the handheld field maintenance tool and the position of such devices can be uploaded to the asset management system. In embodiments where the handheld field maintenance tool may not have ready-access to an asset management system, the handheld field maintenance tool itself may simply store and maintain an asset tracking database that stores field device location information and subsequently synchronize with a personal computer-based asset management application.

While any and all field devices may be mapped, or otherwise have their physical position determined and stored, other process devices and/or fixtures may also be similarly mapped. Essentially, any device or asset in a process installation can be assigned an icon and position in this way. For instance, a large piece of equipment such as a tank can be captured as a reference point on the map. In such a scenario, the asset database within the asset management application and/or the handheld field maintenance tool is required since the tank will not necessarily communicate in accordance with a process industry communication protocol.

In order to further facilitate location-based field maintenance, an individual field device's connection to the rest of the process communication bus/network (for example, Spur block) can be captured and stored in the field device, or the asset database as a setup connection point coordinates. These coordinates may include the standard GPS coordinates for locating the connection hub (longitude, latitude, altitude) and a potential a fourth parameter (terminal number or terminal identification) that is used by a field technician to determine which terminal connection was used to connect/power the field device.

Figure 4:
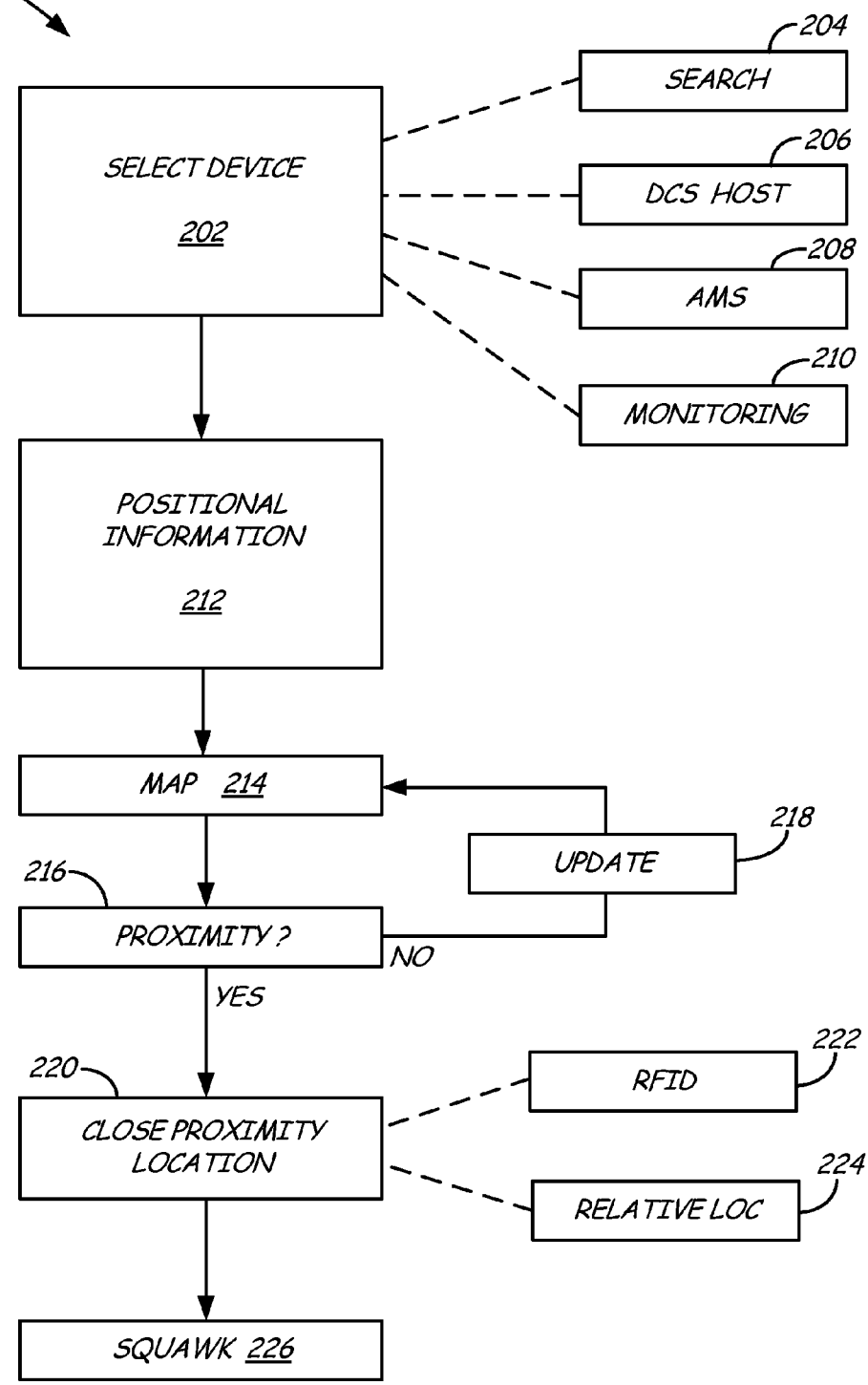
FIG. 4 is a flow diagram of a method of locating a field device in accordance with an embodiment of the present invention.

FIG. 4 is a flow diagram of a method of locating a field device in accordance with an embodiment of the present invention. Method 200 begins at block 202 where a field device is selected. The selection of a field device can be in the form of the user or technician initiating a search 204 for the field device's asset tag. Additionally, if the user is using, or has access to, an application such as a DCS host 206, asset management system 208, or handheld monitoring application 210, the user or technician may be able to invoke a context-sensitive menu, such as by right clicking on a field device, to select the field device.

Once a particular field device is selected, positional information for the selected field device is obtained at block 212. As set forth above, this positional information may be stored locally in a handheld field maintenance tool, or stored in a database in an asset management system. Further, the positional information may even include handwritten records or notes. Regardless, the positional information obtained at block 212 is provided to a handheld field maintenance tool, and a map is generated at block 214. Preferably, the map is initially centered upon the field device indicated by the positional information. The current position of the handheld field maintenance tool is then used to render an icon or representation of the handheld field maintenance tool position relative to the selected field device. This is merely a preferred embodiment, since it is also contemplated that the handheld field maintenance tool can be the center of the map. Preferably, the map is preferably referenced to North, or referenced based upon the current heading of the handheld field maintenance tool as indicated by compass module 152. Preferably, the scale of the map is automatically selected such that the initial rendering of the map places the handheld field maintenance tool near an edge of the map with the selected field device at the center of the map, or vice versa. Additionally, a background picture is preferably used to provide scale. For example, a satellite view of the process installation can be used. However, any suitable pictorial representation of the process installation generated or obtained from blueprints or CAD drawings may be used in addition to, or in place of, a satellite view. Finally, an aerial view taken from an airplane could also be used for the background picture of the map.

Preferably, the user interface provides the technician with the ability to manipulate the map by zooming in to show more detail, and zooming out to show more landmarks. Alternatively, the background picture can be a reference asset image to show the technician an example appearance of the field device for which he or she is searching.

Once the map is rendered, or otherwise displayed, the technician will begin to physically journey into the field to locate the selected field device or process asset. As the handheld field maintenance tool detects the change in the technician's position, the handheld field maintenance tool repeatedly tests whether the technician is within a selected proximity 216 of the field device. If the technician has not achieved a selected proximity to the field device, the map is continually updated, as indicated at block 218, and the loop continues until the technician reaches a selected proximity of the field device. Upon reaching the selected proximity of the field device, block 220 executes where close proximity location of the field device is initiated.

Generally locating a field device amongst a group of field devices confined to a small geographic area is difficult with simply the GPS/cellphone/WirelessHART location options. In order to further assist the technician once a selected proximity has been achieved, at least two close proximity location options are provided. The first close proximity location option is based upon RFID tags. RFID tags use near-field communication to exchange information between a tag and a reader. RFID tags are quite useful, but generally require close proximity to the RFID reader. Active RFID tags have a longer range, yet require a battery and are somewhat more expensive. As indicated in FIG. 3, RFID module 128 can be used to interact with RFID tags in the selected field device to achieve close proximity location. A second option for close proximity location is relative location coordinates 224. Relative location coordinates include a pair of numbers (1, 1) to (255, 255) and a description of the reference point from the perspective of someone standing South of the reference and facing North toward the reference. For instance, a wellhead (face North) may be the reference point. Once again, the map is preferably created where the visible devices are fully visible (i.e. not transparent). Devices hidden from view by the wellhead or other equipment are preferably transparent. A coordinate of (1, 1) would be the upper left hand corner of the technician's viewing area and a coordinate of (255, 255) would be the lower right hand corner of the viewing area. If a camera is installed on the handheld field maintenance tool, a picture could also be taken to show the viewing area. Once the technician has located the field device using close proximity location 220, the location is preferably verified. One way in which the located device could be verified is the presence or reference to the physical tag of the field device. In some instances, this may not be possible if the tag has become damaged or corroded to some extent. Preferably, the field device is installed with a jumper or button, or other suitable circuit that can be accessed by the field maintenance technician locally to generate a squawk message 226 to broadcast on the field device's native process communication loop or segment using the field device's native process communication protocol. The handheld maintenance tool used by the technician then listens to the process communication loop/segment for the squawk signal or message to confirm that the correct device has generated the squawk before maintenance on that device is performed by the technician.

Figure 5:
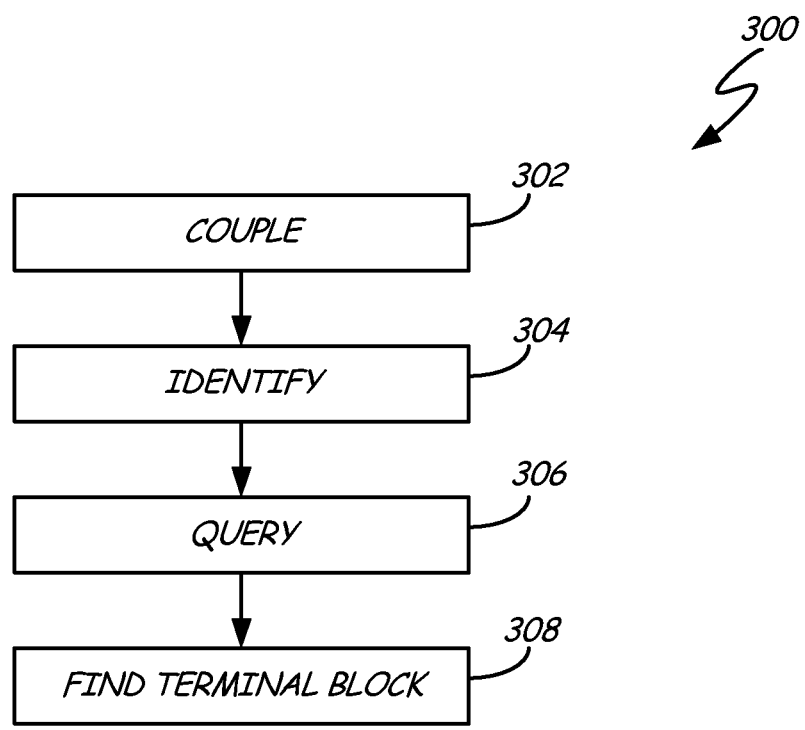
FIG. 5 is a flow diagram of a method of performing location-assisted field maintenance in accordance with an embodiment of the present invention.

FIG. 5 is a flow diagram of a method of performing location-assisted field maintenance in accordance with an embodiment of the present invention. Method 300 begins at block 302 where a handheld field maintenance tool is communicatively coupled to a process communication loop or segment. Next, at block 304, the handheld field maintenance tool communicates over the process communication loop or segment to identify all field devices on the process communication loop or segment. At block 306, the handheld field maintenance tool queries each field device to obtain its physical location or coordinates as well as the terminal number that connects the field device to the process communication loop or segment. Preferably, the location or coordinates of the terminal are also provided to the handheld field maintenance tool by the field device. At block 308, the handheld field maintenance tool provides an indication to the technician relative to a terminal. In this way, the technician may ensure that the correct field device is disconnected from the terminal when it is maintained without the necessity of tracing back the wires.

Figure 6:
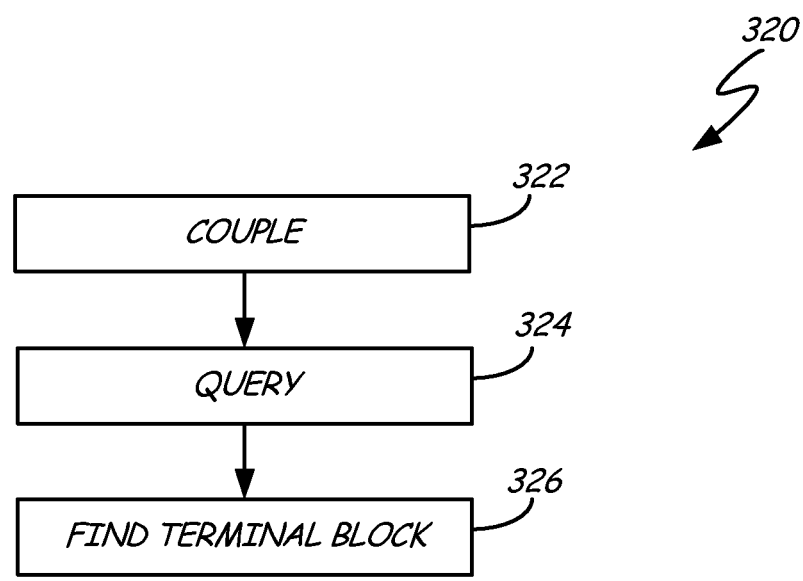
FIG. 6 is a flow diagram of a method of performing location-assisted field maintenance in accordance with an embodiment of the present invention.

FIG. 6 is a flow diagram of a method of performing location-assisted field maintenance in accordance with an embodiment of the present invention. Method 320 begins at block 322 where a handheld field maintenance tool is communicatively coupled to a field device. Next, at block 324, the handheld field maintenance tool queries the field device to obtain its terminal block location. At block 326, the handheld field maintenance tool provides a map, or other suitable indication, to the technician via display 120 to guide the technician to the location of the terminal block of the field device.

Figure 7:
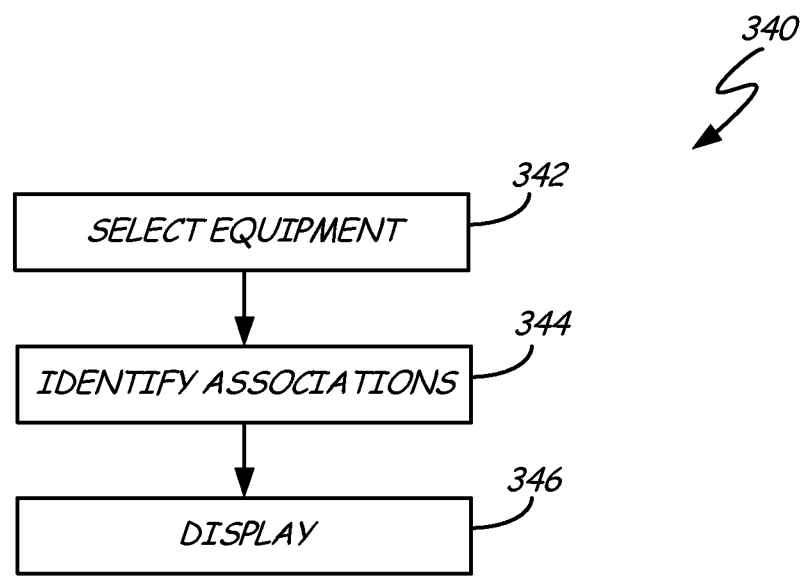
FIG. 7 is a flow diagram of a method of performing location-assisted field maintenance in accordance with an embodiment of the present invention.

FIG. 7 is a flow diagram of a method of performing location-assisted field maintenance in accordance with an embodiment of the present invention. Method 340 begins at block 342 where a technician selects a particular process asset or piece of equipment using a handheld field maintenance tool. Next, at block 344, the handheld field maintenance tool queries a local database, or a remote asset management system, to identify all field devices and/or process installation assets that are associated with the selected process asset or piece of equipment. At block 346, the handheld field maintenance tool displays all associated devices and assets on a map for the technician. In this way, the technician can easily find and interact with the various field devices and assets that are associated with the selected process asset.

Although the present invention has been described with reference to particular embodiments, workers skilled in the art will recognize that changes may be made in form and detail without departing from the spirit and scope of the invention.

What is claimed is:

1. A handheld field maintenance tool comprising:
    a wireless process communication protocol module configured to communicate in accordance with a wireless process communication protocol;
    a display;
    an input device; and
    a controller coupled to the wireless process communication protocol module, the display, and the input device, the controller being configured to generate a map on the display indicating a physical position of the handheld field maintenance device relative to a physical position of at least one asset, wherein the controller is further configured to determine a physical position of the handheld field maintenance device by triangulating using wireless process communication with a number of wireless field devices, each having a known, fixed physical position.

2. The handheld field maintenance tool of claim 1, wherein the at least one asset includes a field device.

3. The handheld field maintenance tool of claim 1, and further comprising a GPS module coupled to the controller, the GPS module configured to receive satellite GPS signals to determine a position of the handheld field maintenance tool.

4. The handheld field maintenance tool of claim 1, wherein the controller provides an indication of the asset in a center of the map.

5. The handheld field maintenance tool of claim 4, wherein the indication of the asset is an icon.

6. The handheld field maintenance tool of claim 5, wherein a parameter of the icon varies with a parameter known relative to the asset.

7. The handheld field maintenance tool of claim 6, wherein the parameter of the icon is transparency, and the parameter known relative to the asset is height relative to ground level.

8. The handheld field maintenance tool of claim 1, wherein the handheld field maintenance tool is intrinsically-safe.

9. A method of locating a field device using a handheld field maintenance tool, the method comprising:
    selecting a field device to locate;
    accessing position information relative to the selected field device;
    determining a current physical position of the handheld field maintenance tool; and
    generating a map on a display of the handheld field maintenance tool showing the current physical position relative to the accessed position information relative to the selected field device, wherein a physical position of the field device is centered on the map.

10. The method of claim 9, and further comprising updating the map as the current position changes, and determining if the current position is within a selected threshold of the field device.

11. The method of claim 10, wherein a close proximity location function of the handheld field maintenance tool when the selected threshold has been reached.

12. The method of claim 11, and further comprising verification of the field device by local access to the field device.

13. The method of claim 12, wherein local access includes causing the field device to generate a signal over its process communication loop/segment and using the handheld field maintenance tool to verify the signal.

14. The method of claim 9, wherein an icon of the field device is displayed with a parameter that indicative of a known parameter of the field device.

15. The method of claim 14, wherein the parameter of the icon is transparency and the parameter of the field device is height relative to ground level.

16. The method of claim 9, wherein the handheld field maintenance tool complies with an intrinsic safety specification.

17. A method of locating a field device using a handheld field maintenance tool, the method comprising:
    selecting a field device to locate;
    accessing position information relative to the selected field device;
    determining a current physical position of the handheld field maintenance tool;
    generating a map on a display of the handheld field maintenance tool showing the current physical position relative to the accessed position information relative to the selected field device;
    updating the map as the current physical position changes; and
    determining if the current physical position is within a selected threshold of the field device.

18. The method of claim 17, and further comprising executing a close proximity location function of the handheld field maintenance tool when the selected threshold has been reached.

19. The method of claim 18, wherein the close proximity location function employs near-field communication.

20. The method of claim 18, wherein the close proximity location includes providing relative location coordinates.

21. The method of claim 17, wherein the handheld field maintenance tool complies with an intrinsic safety specification.

22. A method of determining a physical location an object using a handheld tool, the method comprising:
   placing the handheld tool in proximity to the object;
   causing the handheld tool to determine a current physical position of the handheld tool;
   receiving a user input indicative of a physical position of the object relative to the current physical position of the handheld tool; and
   storing physical position information relative to the object, wherein the physical position information is based on the current physical position of the handheld tool and the user input.

23. The method of claim 22, wherein the object is an asset in a process installation.

24. The method of claim 23, wherein the process installation asset is a field device.

25. The method of claim 23, wherein the user input includes height of the process installation asset relative to ground level.

26. The method of claim 22, wherein the user input includes height of the object relative to the handheld tool.

27. The method of claim 22, wherein the handheld tool is a handheld field maintenance tool.

28. The method of claim 27, wherein the handheld field maintenance tool complies with an intrinsic safety specification.

29. The method of claim 22, wherein causing the handheld tool to determine a current position includes using GPS signals.

30. A method of identifying a connection hub using a handheld field maintenance tool, the method comprising:
   communicatively coupling the handheld field maintenance tool to a process communication loop or segment having a plurality of field devices coupled thereto;
   using the handheld field maintenance tool to identify all field devices on the segment or loop;
   using the handheld field maintenance tool to query each field device for location information of the connection hub and terminal number relative to the field device; and
   locating a connection hub relative to at least one of the plurality of field devices using the handheld field maintenance tool.

31. A method of identifying a connection hub of a field device using a handheld field maintenance tool, the method comprising:
   communicatively coupling the handheld field maintenance tool to the field device;
   using the handheld field maintenance tool to query the field device for the location of the connection hub relative to the field device; and
   locating a connection hub relative to the field device using the handheld field maintenance tool.

32. A method of indicating field devices using a handheld field maintenance tool, the method comprising:
   receiving an input indicative of a selection of a process installation asset;
   identifying at least one field device associated with the selected process installation asset; and
   providing a map on the handheld field maintenance tool showing a physical location of the selected process installation asset and the at least one associated field device.

* * * * *

UNITED STATES PATENT AND TRADEMARK OFFICE
CERTIFICATE OF CORRECTION

| | | |
|---|---|---|
| PATENT NO. | : 8,766,794 B2 | Page 1 of 1 |
| APPLICATION NO. | : 13/191623 | |
| DATED | : July 1, 2014 | |
| INVENTOR(S) | : Ferguson et al. | |

It is certified that error appears in the above-identified patent and that said Letters Patent is hereby corrected as shown below:

In the Claims

Col 10 line 44 Claim 14:
after "displayed with a parameter that" insert --is--

Col 11 line 12 Claim 22:
after "determining a physical location" insert --of--

Signed and Sealed this
Nineteenth Day of May, 2015

Michelle K. Lee
*Director of the United States Patent and Trademark Office*